United States Patent
De Polo et al.

(10) Patent No.: US 7,806,868 B2
(45) Date of Patent: Oct. 5, 2010

(54) DRUG RESERVOIR LOADING AND UNLOADING MECHANISM FOR A DRUG DELIVERY DEVICE USING A UNIDIRECTIONAL ROTATED SHAFT

(75) Inventors: Marco C. De Polo, San Mateo, CA (US); Christopher Wiegel, Sunnyvale, CA (US); Charles C. Raney, Camdenton, MO (US); Arturo Meuniot, San Francisco, CA (US); Arne Lang-Ree, Los Gatos, CA (US)

(73) Assignees: Roche Diagnostics Operations, Inc., Indianapolis, IN (US), part interest; Disetronic Licensing AG, Burgdorf (CH), part interest ( * ) Notice: Subject to any disclaimer, the term of this patent is extended or adjusted under 35 U.S.C. 154(b) by 42 days.

(21) Appl. No.: 11/948,220

(22) Filed: Nov. 30, 2007

(65) Prior Publication Data

US 2009/0143735 A1   Jun. 4, 2009

(51) Int. Cl.
  *A61M 37/00* (2006.01)
(52) U.S. Cl. .................... 604/155; 604/154; 604/151; 604/131
(58) Field of Classification Search ............. 604/131, 604/151–155
See application file for complete search history.

(56) References Cited

U.S. PATENT DOCUMENTS

| | | | |
|---|---|---|---|
| 2,472,116 A | 6/1949 | Maynes | |
| 2,627,270 A | 2/1953 | Glass | |
| 2,734,504 A | 2/1956 | Crescas et al. | |
| 4,351,332 A | 9/1982 | Whitney et al. | |
| 4,430,079 A | 2/1984 | Thill et al. | |
| 4,493,704 A | 1/1985 | Beard et al. | |
| 4,529,401 A | 7/1985 | Leslie et al. | |
| 4,648,872 A | 3/1987 | Kamen | |
| 5,505,709 A * | 4/1996 | Funderburk et al. | 604/155 |
| 5,954,697 A * | 9/1999 | Srisathapat et al. | 604/155 |
| 6,248,093 B1 | 6/2001 | Moberg | |
| 6,423,035 B1 | 7/2002 | Das et al. | |
| 2006/0206054 A1 | 9/2006 | Shekalim | |
| 2008/0077081 A1 * | 3/2008 | Mounce et al. | 604/67 |

FOREIGN PATENT DOCUMENTS

WO   2005094921   10/2005

* cited by examiner

Primary Examiner—Nicholas D Lucchesi
Assistant Examiner—Leah Stohr
(74) Attorney, Agent, or Firm—Dinsmore & Shohl LLP

(57) ABSTRACT

A drug reservoir loading and unloading mechanism for drug delivery device using unidirectional rotated lead screw and method thereof are disclosed. The drug reservoir loading/unloading mechanism allows exchanging the drug reservoir quickly with very few steps and with more safety. The invention neither requires rewinding of the drive system either automatically or manually while replacing the drug reservoir nor requires an additional adapter to secure the drug reservoir.

16 Claims, 5 Drawing Sheets

DRUG RESERVOIR LOADING AND UNLOADING MECHANISM FOR A DRUG DELIVERY DEVICE USING A UNIDIRECTIONAL ROTATED SHAFT

FIELD OF THE INVENTION

The present invention is related to drug delivery devices, and in particular to a drug reservoir loading and unloading mechanism for a drug delivery device using a unidirectional rotated shaft.

BACKGROUND OF THE INVENTION

Conventional portable drug delivery systems are driven typically by a lead screw mechanism that displaces a plunger of a drug reservoir to deliver the medication. The drug reservoir is embedded usually in a compartment, in which the plunger of the drug reservoir has to be physically connected to the lead screw or to the nut due to the siphoning effect. This effect can result in an unintended drug delivery when the pulling force of the fluid column in a catheter is higher than the friction force of the plunger.

In drug deliver systems which reuse the lead screw (and the nut), the drug reservoirs are mostly inserted from the top side of the device. Once the drug reservoir is inserted into the device and the plunger is connected to the lead screw, the drug reservoir has to be secured by a lid or by an adapter. In these devices, to insert a new reservoir that is full of fluid, it is necessary to reverse the direction of the lead screw until the piston engagement returns back to the starting position. Thus the drive system must be able to be reversed in direction. On the other hand, in solenoid or non-motor driven systems, the piston engagement must be reset manually when placing a newly filled or partially filled reservoir. Both types of reset methods are problematic in different manners.

For example, in motor rewind configurations, the motor must be capable of being reversed requiring additional switches and have complex circuitry. In addition, piston sensing is required to shut off motor at a home position, which consumes extra battery energy, and it is not possible to accommodate a partially filled cartridge without manually adjusting the drive system. Similarly, manual reset configurations also have inherent problems.

Typically, manual reset configurations require a more complex housing and a sophisticated nut mechanism to manually engage and disengage the threads. In addition, the disengagement mechanism is both difficult and costly to design and manufacture, the mechanism must be safeguarded from any inadvertent actuation, additional wear issues must be considered, and manual dexterity is required to perform proper function.

SUMMARY OF THE INVENTION

It is against the above background that the present invention provides a drug reservoir loading and unloading mechanism for a drug delivery device using a unidirectional rotated shaft. The drug reservoir loading/unloading mechanism allows exchanging the drug reservoir quickly with very few steps and with more safety. For example, the invention does not require rewinding (reversing) of the shaft or drive system either automatically or manually while replacing the drug reservoir.

In one embodiment, a drug delivery device is disclosed and comprises a shaft, and a drive system operably connected to the shaft and configured to only rotate the shaft in a first direction. A drug reservoir having a plunger used to adjust a volume of the drug reservoir is also provided. A piston rod is operably connected at a first end to the plunger and provides threads. The piston rod is operably connected to the shaft, wherein the drug delivery device provides a secured position which permits the rotation of the shaft to drive the piston rod and move the plunger to adjust the volume of the drug reservoir, and an unsecured position which permits the drug reservoir to be removed unobstructed from the drug deliver device and replaced without having to rotate the shaft in a direction opposite to the first direction.

These and other features and advantages of the invention will be more fully understood from the following description of various embodiments of the invention taken together with the accompanying drawings.

BRIEF DESCRIPTION OF THE DRAWINGS

The following detailed description of the various embodiments of the present invention can be best understood when read in conjunction with the following drawings, where like structure is indicated with like reference numerals and in which.

DETAILED DESCRIPTION

In the following description of the embodiments of the invention, skilled artisans appreciate that elements in the figures are illustrated for simplicity and clarity and have not necessarily been drawn to scale. For example, the dimensions of some of the elements in the figures may be exaggerated relative to other elements to help to improve understanding of embodiment(s) of the present invention. Accordingly, the drawings are merely schematic representations, intending to depict only typical embodiments of the invention, and therefore should not be considered as limiting the scope of the invention. The invention will be described with additional specificity and detail through the accompanying drawings.

Figure 1:
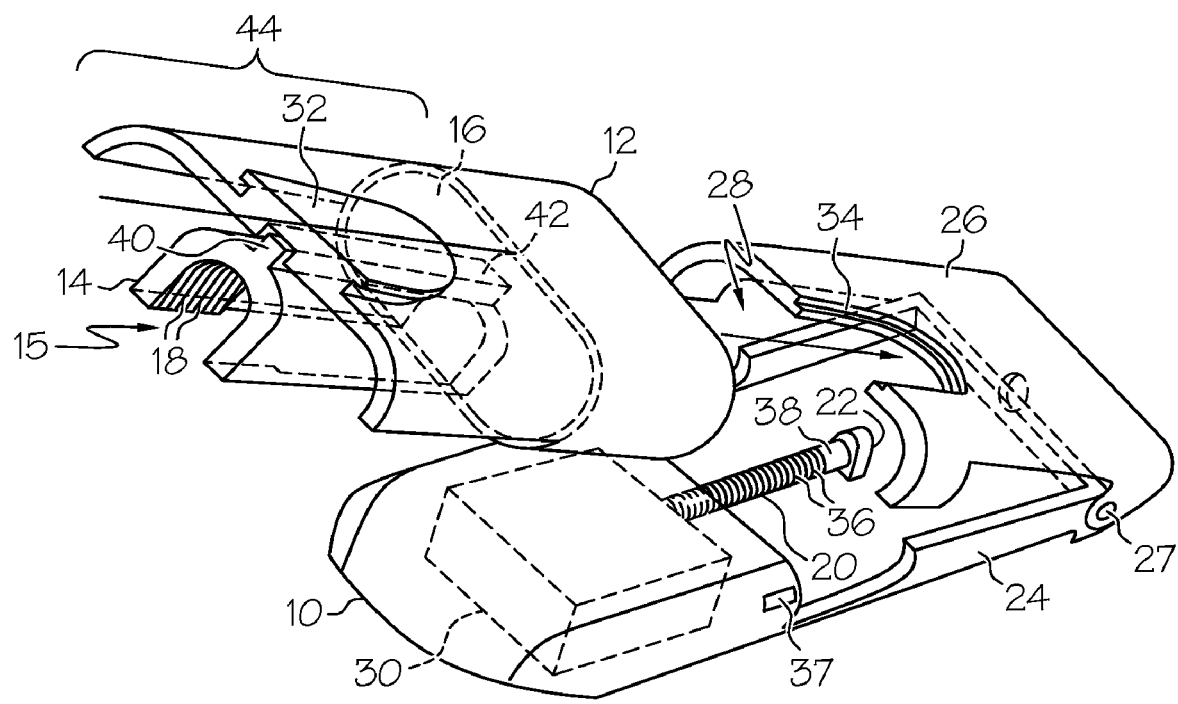
FIG. 1 is a perspective view of one embodiment of a drug delivery device with a disposable drug reservoir according to the present invention.

With reference to FIG. 1, a perspective view of a drug delivery device 10 according to an embodiment of the present invention is shown. In this illustrated embodiment, the drug delivery device 10 provides a disposable drug reservoir 12 having a piston rod 14 connected at one end to a plunger 16 that is used to adjust the volume of the drug reservoir 12 and to dispense a liquid drug contained therein. In one embodiment, the piston rod 14 is shaped to provide a channel or slot 15. In one embodiment, at the free end of the piston rod 14, a flexible nut segment 18 is provided integral with the slot 15 on the inside surface of the piston rod 14. The nut segment 18 is threaded and is engageable with a shaft 20 of the drug delivery device 10.

In the illustrated embodiment of FIG. 1, the shaft 20 of the drug delivery device 10 at one end is mounted for rotation to a shaft support 22 provided to a base 24 of the drug delivery device 10. A lid 26 is mounted pivotally to the base 24, such as for example, by a hinge 27 so that it can be opened and closed manually. Together, the base 24 and the lid 26 define a reservoir compartment, which is generally indicated by symbol 28. The other end of the drive shaft 20 is operably connected to a drive system 30 of the drug deliver device 10, which incrementally and unidirectionally rotates the drive shaft 20 upon activation. The drive system 30 may drive the shaft 20 by a motor actuator or by a limited stroke actuator such as Linear Piezoelectric Motor, Shape Memory Alloy, Piezo Bender, or the like. A ratchet mechanism (not shown) can be used to increase torque and to refine the resolution of the shaft's rotation. Examples of drive systems suitable for use with the present invention are disclosed by commonly owned and co-pending applications U.S. patent application Ser. Nos. 11/874,417; 11/946,905 and 11/936,813, the disclosures of which are herein fully incorporated by reference.

As shown by the illustrated embodiment of FIG. 1, the drug reservoir 12 is inserted at an angle to the shaft 20 into the reservoir compartment 28 of the drug delivery device 10. In one embodiment, the drug reservoir 12 and the lid 26 each provide an engagement feature 32 and 34, respectively, which associates together such the drug reservoir 12 engages first with and is held by the lid 26 while in the open position. In one embodiment, engagement feature 32 of the drug reservoir 12 is a raise portion providing a groove which accommodates slidably the complimentary shaped engagement feature 34 of the lid 26. In such an embodiment, opening and closing the lid 26 disengages and engages, respectively, the nut segment 18 of the piston rod 14 with threads 36 of the shaft 20, which in this embodiment is provided as a lead screw.

It is to be appreciated that opening lid 26 disengages the nut segment 18 from the threads 36 of the shaft 20, and thus the drug reservoir 12 can then be pulled unconstructively out of the reservoir compartment 28. In this manner, it is to be further appreciated that the drug delivery device 10 does not require rewinding of the drive system 30 automatically nor manually when it comes time to replace the drug reservoir 12. In addition, as the nut segment 18 is integral with the drug reservoir 12, thereby making it also disposable, the drug reservoir 12 can be replaced in fewer steps and with higher reliability as compared to drug deliver devices that do not have a nut segment integral with the disposable drug reservoir and/or which require rewinding of the drive system in order to replace the drug reservoir. A locking mechanism 37 may be provided to prevent inadvertent opening of the lid 26.

Figure 2:
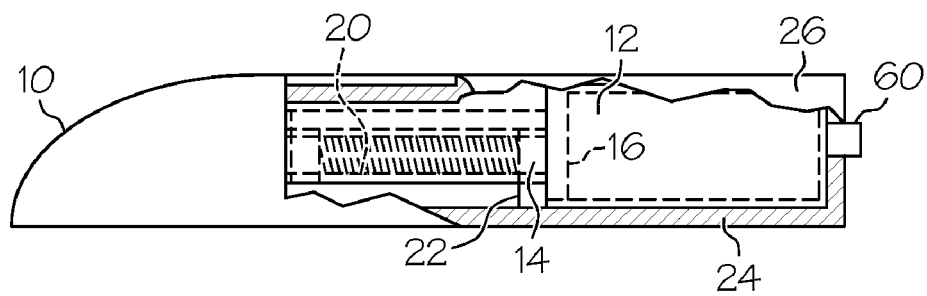
FIG. 2 is a partially sectioned and cut away side view of the drug delivery device of FIG. 1 enclosing the disposable drug reservoir according to the present invention.

Referring also to FIG. 2, the closed position of the lid 26 is shown with the nut segment 18 engaged with the threads 36 of shaft 20. In one embodiment, the nut segment 18 is flexible such that it is snapped over the shaft 20 generally perpendicular to the shaft axis while closing the lid 26, thus engaging with the threads 36. With the lid 26 closed, the drug reservoir 12 fits tightly into the reservoir compartment 28 to avoid backlash of the piston rod 14 which otherwise could cause an unintended drug delivery or under delivery. Accordingly, as the shaft 20 is rotated unidirectionally, due to its engagement with threads 36, the nut segment 18 moves linearly along the shaft 20.

In the illustrated embodiment, an unthreaded portion 38 may be provided on the shaft 20 adjacent the shaft support 22. The nut segment 18 will move linearly as the shaft 20 is rotated until being rotated unto the unthreaded portion 38. At this point, even though the shaft 20 is rotating, the nut segment 18 ceases to advance the piston rod 14 which provides protection to the drive system 30 and the threads 36 of shaft 20 from a hard stop i.e., cessation of rotation due to the nut segment 18 abutting against the shaft support 22, which could cause overheating of the drive system 30 and/or damage to threads 36 due to shredding of the nut segment 18 from over rotation. Furthermore, upon situating the nut segment 18 onto the unthreaded portion 38, the speed and sound of the drive system rotating shaft 20 with change, thus providing an indication that the drug reservoir 12 is empty.

It is to be appreciated that the shaft support 22 in the embodiment shown by FIGS. 1 and 2, is shaped to fit within the interior surface of the slot of the piston rod 14. In this manner, as the shaft 20 is rotated unidirectionally, moving the nut segment 18 linearly along shaft 20, the piston rod 14 will likewise move linearly unobstructed over the shaft support 22. As best shown by FIG. 1, a key portion 40 of the piston rod 14 rides in a guidance track 42 in an extended wall 44 of the drug reservoir 12 to both ensure linear motion and avoid rotational motion of the nut segment 18. The extended wall 44 also provides the engagement feature 32 on an exterior side thereof. Additional embodiments showing alternative drug reservoir loading and unloading mechanisms for a drug delivery device using a unidirectional rotated shaft according to the present invention is now discussed hereafter.

Figure 3:
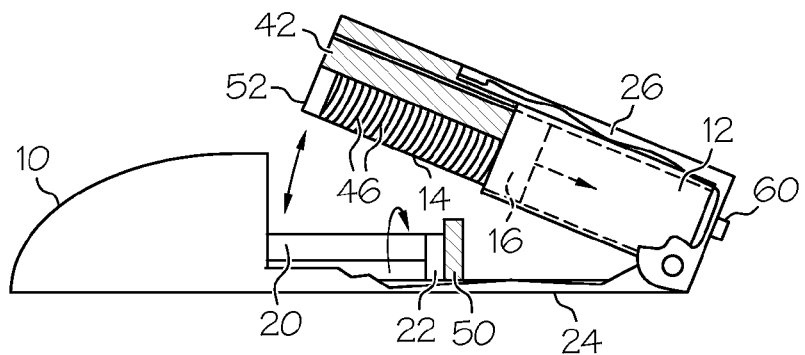
FIG. 3 is a partially sectioned and cut away side view of another embodiment of a drug delivery device shown holding a disposable drug reservoir in a lid thereof, positioned open, according to the present invention.

With reference to the embodiment shown by FIG. 3, portions of the lid 26 are cut away to show the drug reservoir 12 being held in the lid 26 in the open position and inside the drug reservoir compartment 28. In addition, portions of the extended wall 44 and the piston rod 14 are sectioned away to show that in this embodiment, the interior surface of the slot of the piston rod 14 provides threads 46, instead of a nut segment 18 as in the previous embodiment shown by FIG. 1. A gear 48 is mounted to at the end of the shaft 20 adjacent the shaft support 22, and provides threads 50 which mesh with the threads 46 of the piston rod 14. As also with the embodiment show by FIG. 1, the opening and closing of the lid 26 disengages and engages, respectively, the threads 46 of the piston rod 14 with the threads 50 of gear 48. Accordingly, in the closed position, unidirectional rotation of the shaft 20 with cause similar rotation of gear 48, and likewise linear movement of the piston rod 14. As also in the previous embodiment, an unthreaded portion 52 may be provided to the interior surface of the slot of the piston rod 14 to provide protection against a hard stop to the movement of the piston rod 14.

Figure 4:
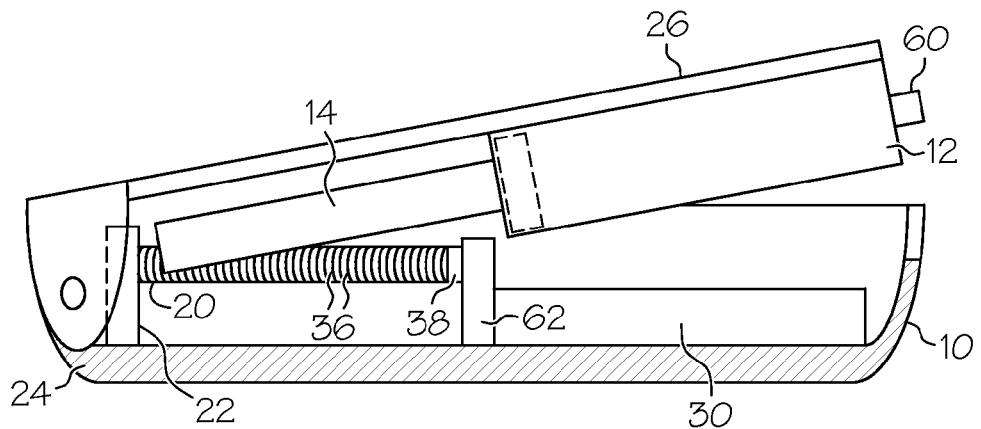
FIG. 4 is a partially sectioned and cut away side view of still another embodiment of a drug delivery device shown holding a disposable drug reservoir in a lid thereof, positioned open, according to the present invention.

It is to be appreciated that although in the previous embodiments shown by FIGS. 1-3, the drug reservoir 12 fits into the lid 26 via directing the front end of the drug reservoir (i.e., the end with exit port 60) into the device first, the opposite loading direction is also envisioned. For example, as illustrated by FIG. 4, in this embodiment the drug reservoir 12 is fitted into the lid 26 with the piston rod 14 being directed in first when the lid 26 is in the open position. In this embodiment, side wall portions of the base 24 are cut away to show that the drug reservoir 12 is held in the lid 26 in the open position as well as the inside of the drug reservoir compartment 28. As in the previous embodiment shown by FIG. 1, the shaft 20 has threads 36, and is provided as a lead screw. As also with the embodiment show by FIG. 1, the threads 36 of the shaft 20 mesh with threads provided on the piston rod 14 such that unidirectional rotation of shaft 20 causes the piston rod 14 to travel away from the shaft support 22 towards a second shaft support 62. As the piston rod 14 linearly moves, the plunger 16 is pushed, thereby adjusting the volume of the drug reservoir 12 and dispensing a liquid drug therefrom.

It is to be appreciated that the second shaft support 62 in the embodiment shown by FIG. 4 is shaped to fit within the interior surface of the slot 15 of the piston rod 14. In this manner, as the shaft 20 is rotated unidirectionally, the piston rod 14 will likewise move linearly unobstructed over the second shaft support 62. However, unlike the embodiment shown by FIG. 1, features such as the key portion 40, the guidance track 42, and the extended wall 44 of the drug reservoir 12 are not provided in this embodiment of the drug reservoir 12 to ensure linear motion. Ensuring linear motion is helped in an alternative manner, which is explained hereafter.

Figure 5:
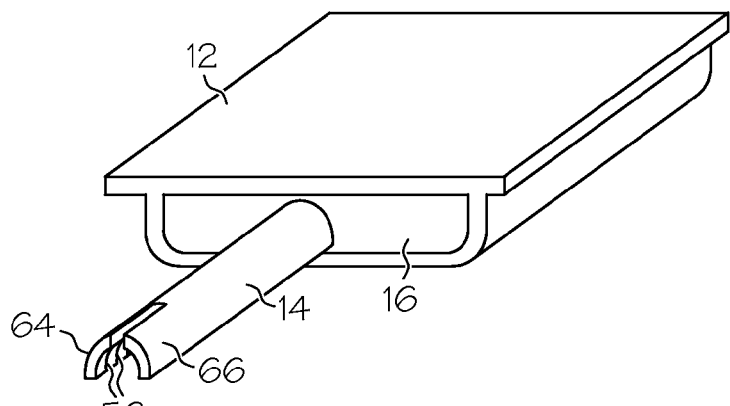
FIG. 5 is an upper perspective view of another embodiment of disposable drug reservoir according to the present invention, which is suitable for use in the drug delivery device shown by FIG. 4.

As shown by FIG. 5, in this embodiment the end of the piston rod 14 of the drug reservoir 12 is split into two portions 64 and 66. In this manner, any misalignment of the threads 56 of the piston rod 14 will cause one of the split portions 64 and 66 to flex. Flexing of the misaligned split portions helps to bring the threads 56 of the piston rod 14 into alignment when being rotated by the shaft 20, thereby helping to ensure proper linear movement of the piston rod 14. In this embodiment the opening and closing of the lid 26 disengages and engages, respectively, the threads 56 of the piston rod 14 with the threads 36 of shaft 20. As also in the previous embodiments, the unthreaded portion 38 may be provided to the shaft 20 adjacent the second shaft support 62 to provide protection against a hard stop. Other opening and closing arrangements and shapes for the drug delivery device is also envisioned, which are discussed hereafter.

Figure 6:
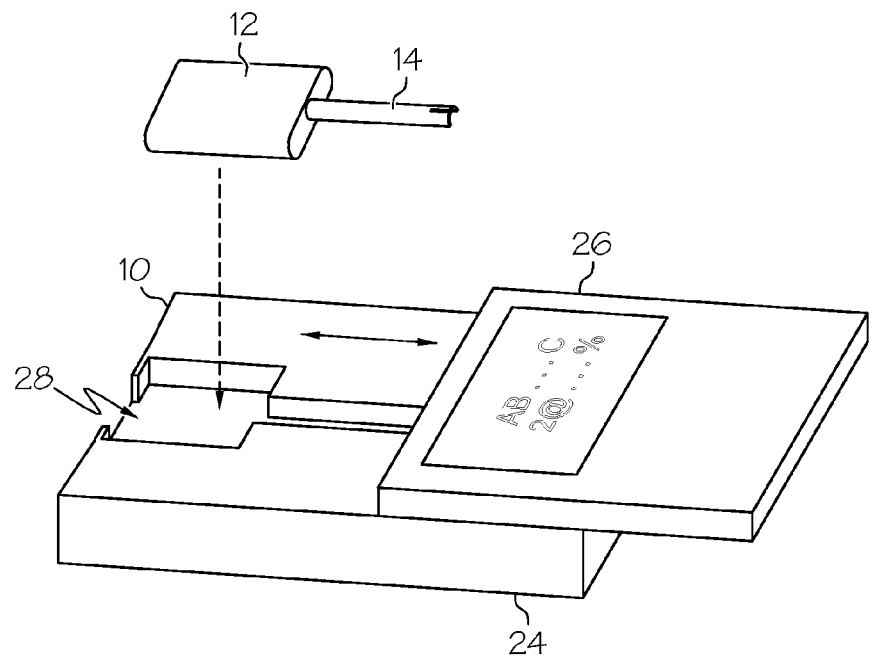
FIG. 6 is an upper perspective view of another embodiment of a drug deliver device and a disposable drug reservoir suitable for use therewith according to the present invention.

In the illustrated embodiment of FIG. 6, the lid 26 of the drug delivery device 10 is a slidably attached to the base 24. As shown, the drug reservoir 12 is shaped to drop substantially perpendicular into the reservoir compartment 28. Sliding the lid 26 over the drug reservoir 12 locks the drug reservoir 12 in the reservoir compartment 28 which protects it from shocks and impacts. By sliding the lid 26 back and forth, the threads of the piston rod 14 will engage/disengage the threads of the shaft (not shown) as in previous embodiments.

Figure 7:
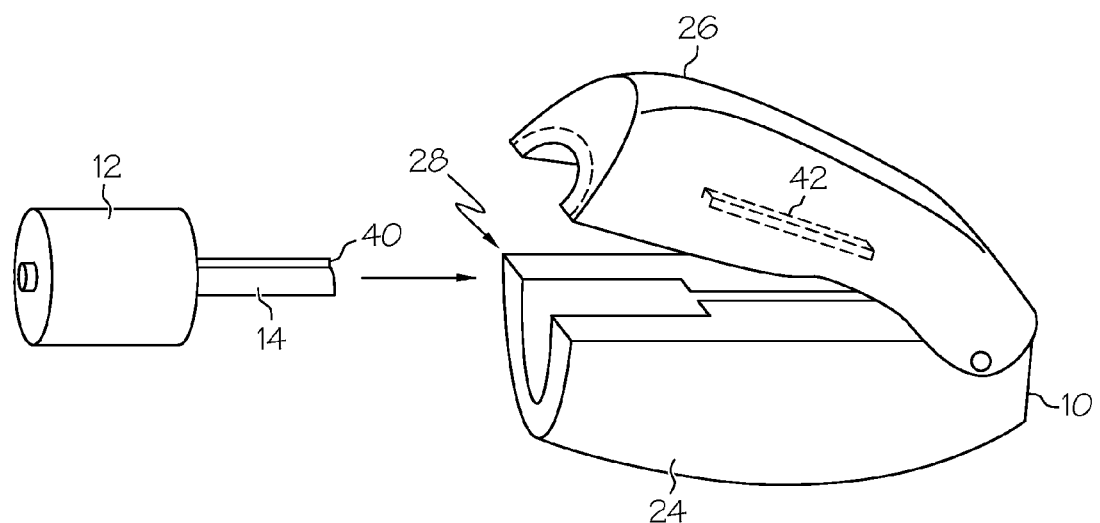
FIG. 7 is an upper perspective view of still another embodiment of a drug deliver device and a disposable drug reservoir suitable for use therewith according to the present invention.

In the alternative embodiment of FIG. 7, the lid 26 opens rotatably, like a clam shell, wherein the guidance track 42 is provided in the lid 26. The drug reservoir 12 accordingly provides the key portion 40 on the piston rod 14 which is accommodated slidably into the guidance track 42 when the lid 26 is closed. As also shown by this embodiment, the drug reservoir is cylindrical in shape and is loaded straight (i.e., not at an angle) into the reservoir compartment 28. After opening the lid 26, the drug reservoir may be removed in a similar manner. As the piston rod 14 engages the shaft 20 of the drug delivery device 10 according to any of the embodiments discussed previously above, for brevity no further discussion regarding this embodiment is provided.

Figure 8:
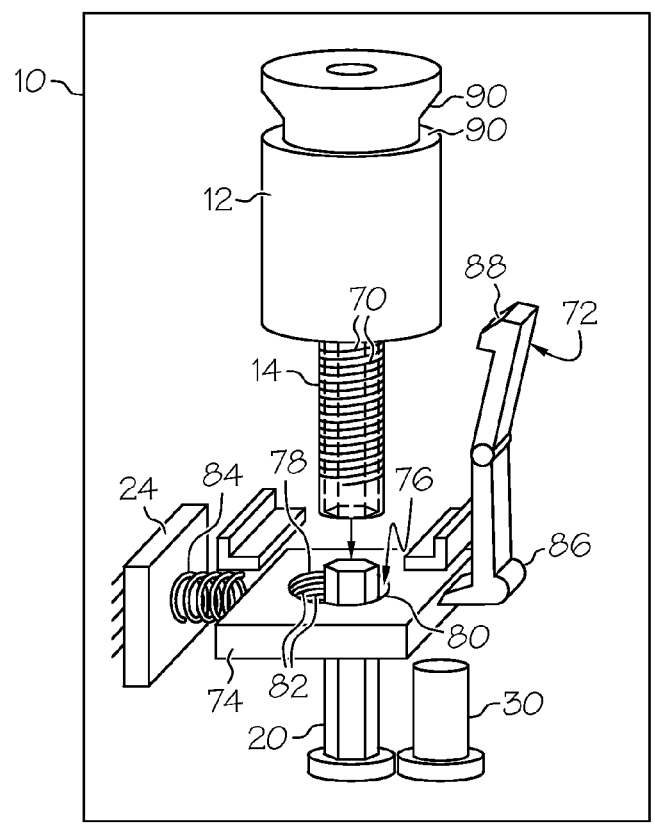
FIG. 8 is an upper perspective view of yet another embodiment of a drug deliver device and a disposable drug reservoir suitable for use therewith according to the present invention.
Figure 9:
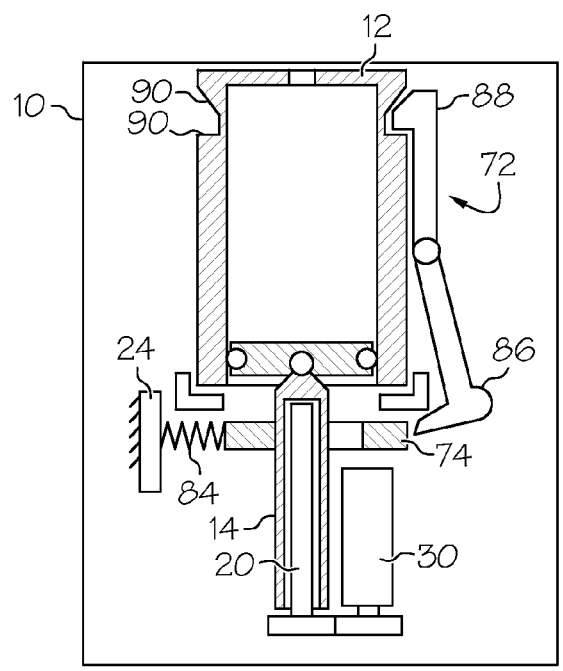
FIG. 9 is a partially section view of the drug deliver device of FIG. 8 shown with the disposable drug reservoir, also sectioned, locked therein.
Figure 10:
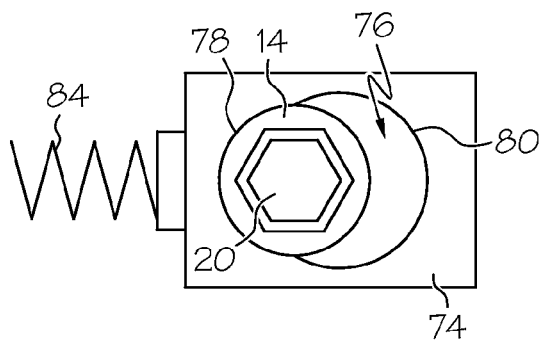
FIGS. 10 and 11 are top views of a partially threaded nut using in the drug deliver device of FIG. 8 according to the present invention.
Figure 11:
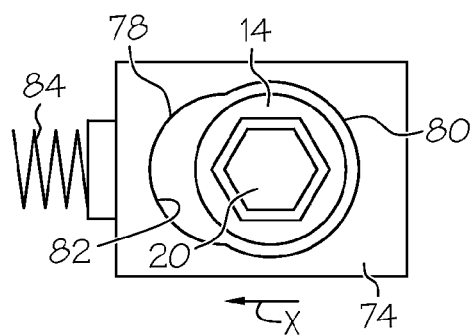

Turning now to FIGS. 8 and 9, a further alternative embodiment of the present invention is shown, with the drug deliver device 10 illustrated in block diagram for ease of illustration. It is to be appreciated that this alternative embodiment is suitable for use in any of the previously illustrated drug deliver device embodiments. In this embodiment, the drug reservoir 12 is generally cylindrical in shape, and the piston rod 14 thereof is moved by the unidirectionally rotated shaft 20 as in all the previous embodiments to push the plunger 16 and adjust the volume of the drug reservoir 12. However, unlike the other previous mentioned embodiments in which the piston rod 14 provides a U-shaped channel or slot and is fixed to the plunger 16, in this embodiment the piston rod 14 is shaped as a hollow cylinder which is rotatably mounted to the plunger 16, such as for example, via ball joint 68 (FIG. 9). The shaft 20 in this embodiment provides a non-cylindrical shape and size to slid into the hollow interior of the piston which is also provides a similar non-cylindrical shape, and which is best shown by FIGS. 10 and 11. In addition, the exterior surface of the piston rod 14 provides threads 70 which are discussed further hereafter.

In the illustrated embodiment, the drug delivery device 10 provides a self locking lever mechanism 72 which performs a first function of securing the drug reservoir 12 to the drug delivery device 10. Another function of the lever mechanism 72, in addition to locking the drug reservoir 12 in place, is to engage/disengage the threads 70 of the piston rod 14 via a partially threaded nut 74. As best shown by FIG. 8, the partially threaded nut 74 has a cavity 76 with a generally keyhole shape having a pair of connected and different sized arc portions 78 and 80, where the smaller arc portion 78 carries threads 82 and the larger arc portion 80 is without threads. In addition the partially threaded nut 74 is biased by a spring 84 that is mounted the base 24 of the drug delivery device 10. As shown, by FIG. 10, the spring 84 normally pushes the threads 82 of the partially threaded nut 74 into engagement with the threads 70 of piston rod 14 when situated through the cavity 76.

A button portion 86 of the lever mechanism 72 is provided which when pushed unlocks a locking portion 88 of the lever mechanism 72 from a catch 90 provided in the drug reservoir 12 and disengages the threads 70, 82 simultaneously, as shown by FIG. 11. In other words, when pushing the button portion 86, the small arc portion 78 of the partially threaded nut 74 is displaced, such that the larger arc portion 84 is situated around the piston rod 14 unengaged. In this manner the drug reservoir 12 may be replaced by pushing down on the button portion 86, as indicated by arrow X, and removing the drug reservoir 12 which slides the shaft 20 from its accommodation within the hollow cylinder shape of the piston rod 14. When the button portion 86 is released, the spring once again pushes the threads 82 of the partially threaded nut 74 into engagement with the threads 70 of the piston rod 14, and also self locks the catch 90 of the drug reservoir 12 with locking portion 88. As the shaft 20 is rotated as discussed previously above, via drive system 30, no further discussion is provided.

Figure 12:
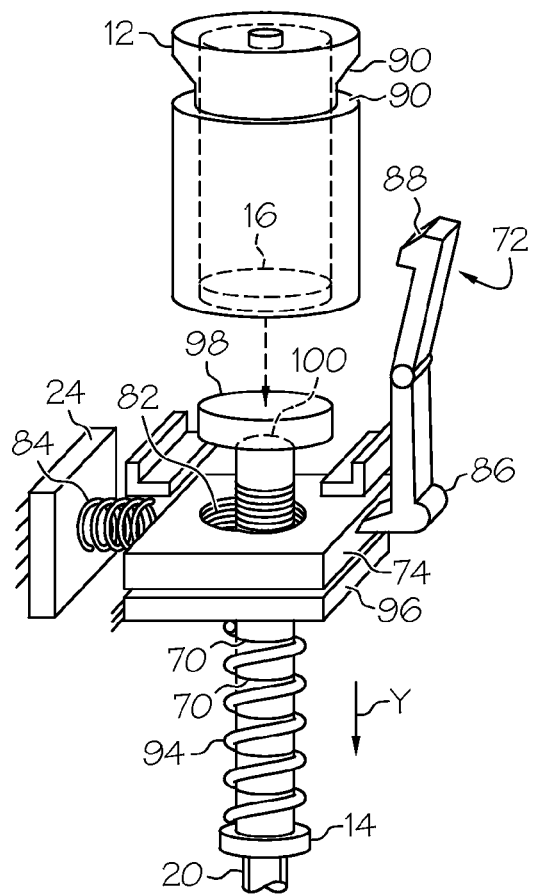
FIG. 12 is an upper perspective view of still yet another embodiment of a drug deliver device and a disposable drug reservoir suitable for use therewith according to the present invention.

With reference to FIG. 12, an alternative embodiment to the embodiment discussed above with reference to FIGS. 9 and 10 is shown, where for brevity, only the differences therebetween are discussed hereafter. In this embodiment, the piston rod 14 does not attached to the plunger 16 of the drug reservoir 12, and thus is not disposable. As before in the embodiment shown by FIG. 8, the shaft is non cylindrical in shape and is slidably accommodated within the piston rod 14. In addition, the threads 70 engage/disengage with the threads 82 of the partially threaded nut 74 via the lever mechanism 72 as also previous mentioned above. However, in this embodiment, the piston rod 14 is axially spring loaded via axial spring 94. As shown, the axial springs 94 biases the piston rod 14 away from a spring mount 96 as indicated by arrow Y. It is to be appreciated that spring loading the piston rod 14 in this manner ensures physical contact between a disc 98 that is rotatably connected to the piston rod 14 and the plunger 16 of the drug reservoir 12, such as for example, by ball joint 100.

Accordingly, as the shaft 20 is rotated unidirectional, with threads 70 and 82 engaged, the piston rod 14 will similarly rotate and advance the disc 98 into contact with the plunger 16, thereby dispensing a liquid drug from the drug reservoir 12 and compressing axial spring 94. Upon depressing the button portion 86 of the lever mechanism 72, such as to remove the drug reservoir 12 from the drug delivery device 10, the piston rod 14 is sprung back via axial spring 94 to a starting position which places the disc 98 closely adjacent the partially threaded nut 74. As the shaft 20 is rotated as discussed previously above, such as via drive system 30, no further discussion is provided.

Although not limited thereto, the following advantages and features of the various embodiment of the present invention are noted. The present invention does not require a cap to secure and lock the cartridge which provides more user convenience due to the fact that there are fewer parts to assemble. The replacement procedure can be done with few steps and therefore within a shorter time. Due to the fact that there are fewer parts to assemble, malfunctions are less likely to occur. There is no rewind function necessary since the piston rod is either disposable with the drug reservoir or is supported by a spring to ensure tight connection between the plunger and the piston rod. Unintended drug delivery due to siphoning i.e., pulling force of a water column that is higher than the friction force of the plunger which results in a low pressure in the reservoir thereby causing unintended drug delivery in case that the plunger is not secured to the lead screw, is not of concern since in one embodiment the disposable piston rod with threads is permanently attached to the plunger of the reservoir. In the embodiment where the plunger is spring biased and not disposable, since a connection to the plunger is not provided, the water column force will be less than the friction force of the plunger, thereby again helping to prevent any unintended drug delivery due to siphoning.

The foregoing description of the invention has been presented for purposes of illustration and description. It is not intended to be exhaustive or to limit the invention to the precise form disclosed, and other modifications and variations may be possible in light of the above teachings. The above embodiments disclosed were chosen and described to explain the principles of the invention and its practical application to thereby enable others skilled in the art to best utilize the invention. It is intended that the appended claims be construed to include other alternative embodiments of the invention except insofar as limited by the prior art.

What is claimed is:

1. A drug delivery device comprising:
    a shaft;
    a drive system operably connected to the shaft and configured to only rotate the shaft in a first direction;
    a disposable drug reservoir having a first engagement feature and a plunger used to adjust a volume of the drug reservoir;
    a piston rod operably connected at a first end to the plunger and providing threads, the piston rod being operably connected to the shaft, wherein said drug delivery device provides a secured position which permits the rotation of the shaft to drive the piston rod and move the plunger to adjust the volume of the drug reservoir, and an unsecured position which permits the drug reservoir to be removed unobstructed from the drug deliver device and replaced without having to rotate the shaft in a direction opposite to the first direction;
    a base which defines a compartment to hold the drug reservoir; and
    a lid having a second engagement feature which engages with the first engagement feature of the drug reservoir, said lid being mounted pivotably to the base and providing open and closed positions wherein when in the closed position the drug reservoir is enclosed by the lid within the compartment of the base to place the drug deliver device in the secured position, and when in the open position the engagement between the first and second engagement features holds the drug reservoir to the lid such that the drug reservoir is held out from the compartment to place the drug deliver device in the unsecured position.

2. The drug delivery device according to claim 1, wherein the piston rod provides a slot and is connected at one end to the plunger.

3. The drug delivery device according to claim 1, wherein the piston rod provides at a second end a flexible nut segment which carriers the threads.

4. The drug delivery device according to claim 1, wherein the piston rod is connected at one end to the plunger, and provides at a second end a flexible nut segment which carriers the threads, wherein when in the secured position, threads of the shaft are engaged by the threads of the flexible nut segment.

5. The drug delivery device according to claim 1, wherein the piston rod provides a slot which carriers the threads, wherein the shaft provided a threaded gear which is configured to rotates within the slot when the drug delivery device is in the secured position, and wherein when said drug delivery device is in said unsecured position, said drug delivery device is configured to permit insertion of the drug reservoir an angle other than perpendicular to bring the threads of flexible nut segment into engagement with the threaded gear.

6. The drug delivery device according to claim 1, wherein the piston rod further comprises a key portion, and a guidance track in an extended wall of the disposable drug reservoir in which the key portion moves to ensure linear motion of the piston rod.

7. The drug delivery device according to claim 1, wherein the piston rod further comprises a key portion, and said lid provides a guidance track in which the key portion moves when the drug delivery device is in the secured position to ensure linear motion of the piston rod.

8. The drug delivery device according to claim 1, wherein the first engagement feature of the drug reservoir accommodates slidably the second engagement feature of the lid.

9. The drug delivery device according to claim 1, wherein the first engagement feature of the drug reservoir is a raise portion providing a groove which accommodates slidably the second engagement feature of the lid.

10. The drug delivery device according to claim 1, wherein the first engagement feature of the drug reservoir and the second engagement feature of the lid are complimentary in shape.

11. The drug delivery device according to claim 1, wherein the first engagement feature of the drug reservoir is a raise portion providing a groove which accommodates slidably the second engagement feature of the lid, wherein the first engagement feature of the drug reservoir and the second engagement feature of the lid are complimentary in shape.

12. The drug delivery device according to claim 7, wherein the extended wall of the drug reservoir provides the first engagement feature on an exterior side thereof.

13. The drug delivery device according to claim 12, wherein the first engagement feature of the drug reservoir accommodates slidably the second engagement feature of the lid.

14. The drug delivery device according to claim 12, wherein the first engagement feature of the drug reservoir is a raise portion providing a groove which accommodates slidably the second engagement feature of the lid.

15. The drug delivery device according to claim 12, wherein the first engagement feature of the drug reservoir and the second engagement feature of the lid are complimentary in shape.

16. The drug delivery device according to claim 12, wherein the first engagement feature of the drug reservoir is a raise portion providing a groove which accommodates slidably the second engagement feature of the lid, wherein the first engagement feature of the drug reservoir and the second engagement feature of the lid are complimentary in shape.

* * * * *